STEREOSCOPIC RETINAL CAMERA

BACKGROUND OF THE INVENTION

1. Field of the Invention

The present invention relates to a stereoscopic retinal camera, and more particularly relates to a mechanism to amend a fluctuation of a stereoscopic visual angle or an inter-image pitch or the like which is caused by a difference of a portion to be photographed or a refracting power of an examinee's eye.

2. Description of Related Art

Figure 7:
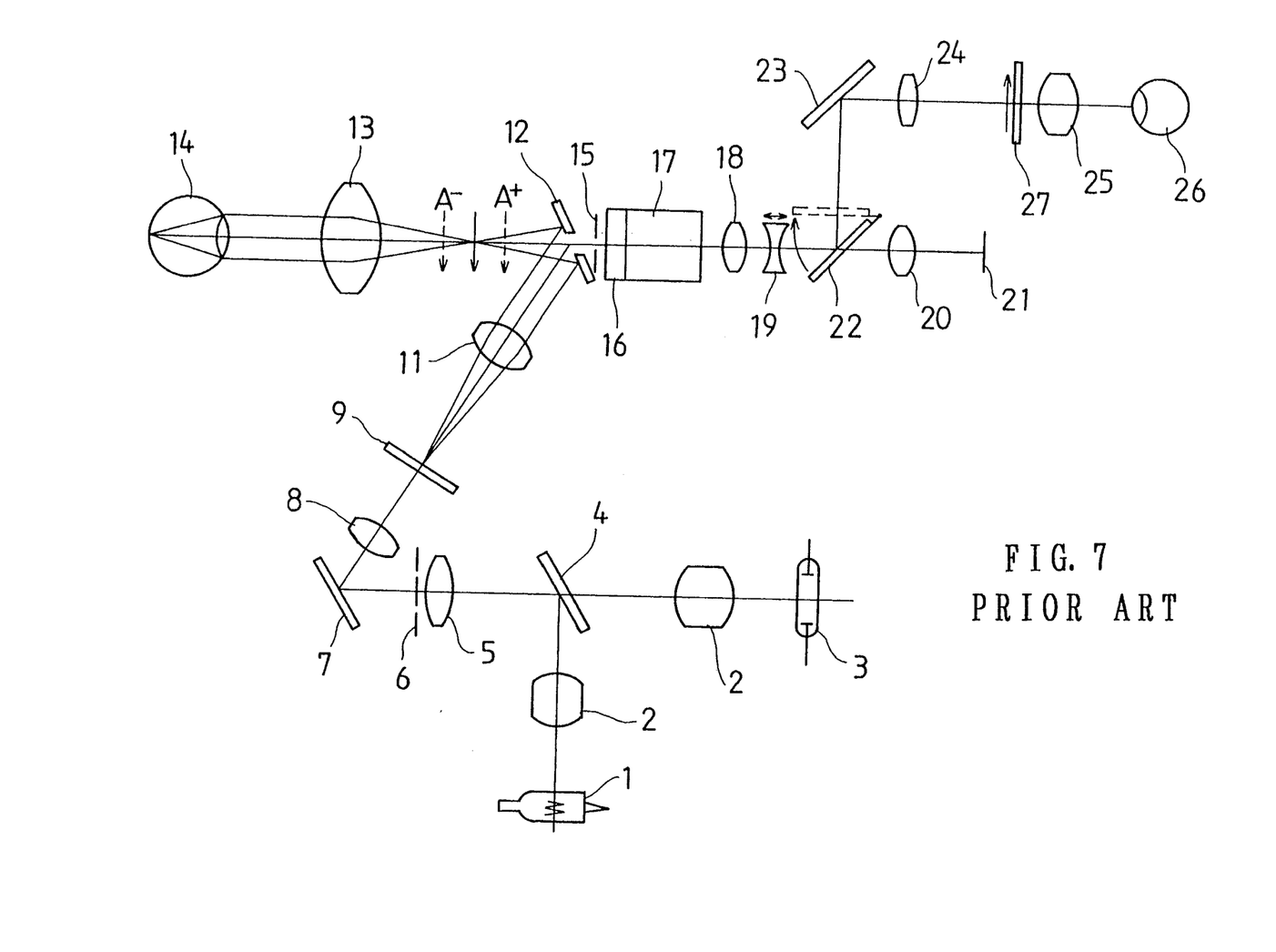
FIG. 7 is a diagrammatic side view of the optical systems of a stereoscopic art retinal camera as one prior art.

A conventional optical system of a stereoscopic retinal camera is as shown in FIG. 7. The construction of the optical system is similar to the system of the embodiment of the present invention which will be mentioned later. In the apparatus of FIG. 7, the light beam reflected by the fundus of an examinee's eye 14 is focused at point A in an inverted image by an objective lens 13, and passing through an aperture of a perforated mirror 12, the light beam is split into two light beams by a two-hole diaphragm 15. The separated light beam is interchanged to a right light beam and a left light beam, the image distance is extended. If there is a defective sight ametropy in the examinee's eye, the photographer moves a focusing lens 19 to a direction of the optical path, so that the fundus image of the eye i s formed on a film 21. In the case of normal eye, the position of the first intermediate image at point A is moved to A⁻side direction along with the optical axis on nearsight, and moved to opposite A⁺side direction on farsight. Therefore, the inter-image pitch on a field stop 27 and a film 21 is changed, whereby a stereoscopic visual angle is changed. This changing is extremely inconvenient for prosecuting a stereoscopic measurement precisely.

Further, there is provided an apparatus which is able to photograph not only eye's fundus, but also a front portion of the eye, in general retinal cameras. Such a kind of apparatus comprises a convex auxiliary lens which is disposed in the photographing optical system insertably. If this kind of mechanism for photographing the front of the eye is adopted on the stereoscopic retinal camera, the stereoscopic visual angle is changed largely, and the inter-image pitch is also changed to small size P' within a range of size P, shown in FIG. 2.

Accordingly, the synthesized area as a stereoscopic image becomes narrow, and a problem is caused in the direct vision of the stereoscopic image.

SUMMARY OF THE INVENTION

The present invention has been made in view of the above circumstances and has an object to overcome the above problems and to provide a stereoscopic retinal camera which can photograph and observe the fundus and/or the front portion of the eye by a certified stereoscopic visual angle, inspire of a defective sight ametropy of the examinee's eye.

The second object of this present invention is to provide a stereoscopic retinal camera which is obtainable a full area of stereoscopic image when the front portion of the eye is photographed from near side.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the stereoscopic retinal camera of this invention comprises a focus adjustment means for photographing each portion of the fundus and the front portion of the eye, and an optical correct means for correcting an inter-image pitch between a right image and a left image so as to be correspondent when the fundus and/or the front portion of the eye is photographed by operating the focus adjustment means.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of one preferred embodiment of a stereoscopic retinal camera embodying the present invention will now be given referring to the accompanying drawings.

Figure 1:
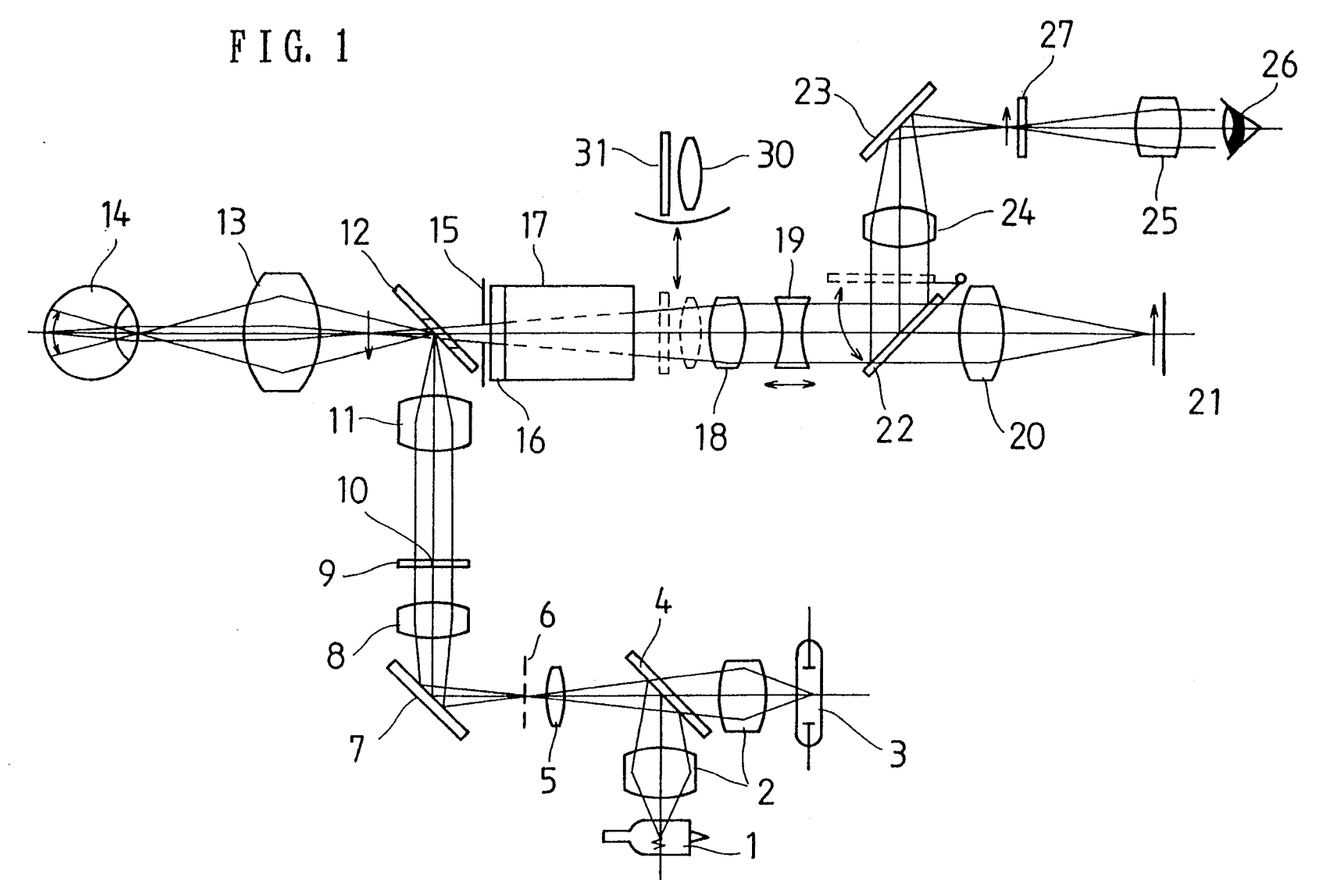
FIG. 1 is a diagrammatic side view of the optical systems of a stereoscopic retinal camera in a first embodiment according to the present invention.

In FIG. 1, there is shown a stereoscopic retinal camera in a first embodiment according to the present invention, which comprises an illuminating optical system, a photographing optical system and an observation optical system.

Illuminating Optical System

The illuminating optical system comprises a halogen lamp 1, i.e., a light source of illumination for observation, condenser lenses 2, a xenon flash lamp 3, i.e., a light source of illumination for photographing, a beam splitter 4, a relay lens 5, an aperture diaphragm 6, a mirror 7 for deflecting an light path, an illuminating relay lens 8, an index plate 9 provided with a central black point 10 for eliminating detrimental light, an illuminating lens 11, a perforated mirror 12 and an objective lens 13. The halogen lamp 1 and the xenon flash lamp 3 are in a conjugate relation with respect to the condenser lenses 2. The aperture diaphragm 6 is provided with a circular slit. An intermediate image of the slit is formed near the opening of the perforated mirror 12, the intermediate image of the slit is reflected by the perforated mirror 12 and the objective lens 13 focuses the image of the slit near the cornea to illuminate the fundus of the eye 14.

Photographing Optical System

Figure 2:
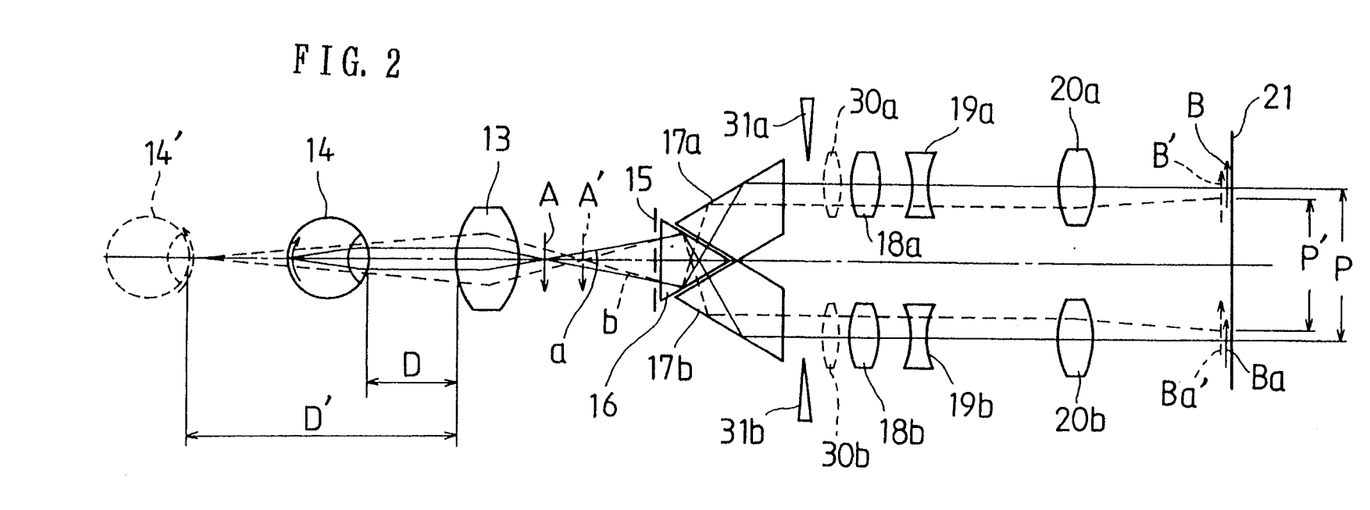
FIG. 2 is a diagrammatic top view of the optical systems of the stereoscopic retinal camera of FIG. 1, which shows a photographing condition that an auxiliary lens 30 is disposed in an optical path of a photographing optical system and a wedge-shaped deflection--angle prism 31 is disposed out of the photographing optical path.

A two-hole diaphragm 15 is in a conjugate relation with the pupil of the eye 14 with respect to the objective lens 13. The two-hole diaphragm 15 splits the light beam into two light beams as shown in FIG. 2. Indicated at 16 and 17 (17a and 17b) are light beam splitting prisms. The light beam splitting prism 16 interchanges a right light beam and a left light beam with each other, and the light beam splitting prisms 17 (17a and 17b) collimate the two light beams so that the collimated light beams pass along two parallel paths separated from each other by a predetermined distance.

The light beam reflected by the fundus of the eye 14 is focused at a point A in an inverted image by the objective lens 13, passes through the opening of the perforated mirror 12, the two-hole diaphragm 15, the light beam splitting prisms 16 and 17 (17a and 17b), relay lenses 18 (18a and 18b), focusing lenses 19 (19a and 19b) and image forming lenses 20 (20a and 20b). The image forming lenses 20 (20a and 20b) form the image of the fundus on the film 21. The focusing lenses 19a and 19b are movable along the optical axis of the photographing optical system. The positions of the focusing lenses 19a and 19b are adjusted according to the refracting power of the eye 14 to focus the image of the fundus on the film 21.

A swing mirror 22 can be turned between a position to reflect the light beam toward the observation optical system and a position to allow the light beam to pass along the optical axis of the photographing optical system to the film 21. In photographing the picture of the fundus, the swing mirror 22 is turned up in the direction of the arrow in synchronism with the flashing action of the xenon flash lamp 3 to allow the light beam reflected by the fundus to fall on the film 21.

Auxiliary lenses 30 (30a and 30b) are disposed in the photographing optical path insertably to change the focusing area from the fundus to the front portion of the eye. In the embodiment of the apparatus, the focus adjusting area formed by the focusing lenses 19a and 19b are provided for photographing the fundus as a center on OD (Zero Diopter), and the area is not enough for photographing the front portion of the eye, which requires strong diopter +D. Accordingly, it is covered by inserting an auxiliary lens which have powers determined based on the position of the above mentioned standard point A'.

Figure 3:
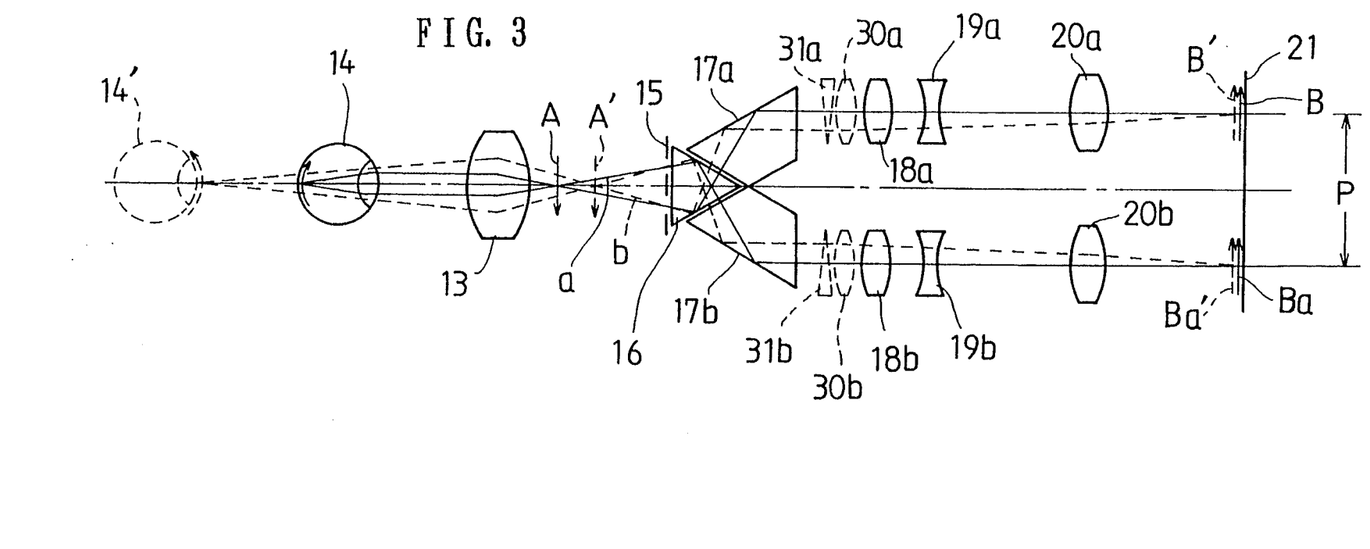
FIG. 3 is a diagrammatic top view of the optical systems of the stereoscopic retinal camera of FIG. 1, which shows a photographing condition that both of the auxiliary lens 30 and the deflection-angle prism 31 are disposed in the photographing optical path.

A thin wedge-shaped deflection-angle prism 31 (31a and 31b) is disposed in the photographing optical path with the auxiliary lenses 30 (30a and 30b) to correct the angle of the optical axis. As shown in FIG. 2, in case of photographing the front portion of the eye, the working distance is extended to D' from D which is the working distance for photographing the fundus. Therefore the intermediate image is moved to A' from A by the objective lens 13, the inter-image pitch P' becomes narrow against the inter-image pitch P for photographing the fundus. The deflection-angle prisms 31a and 31b are inserted into the optical path, the inter-image pitch P is extended (shown in FIG. 3). The degree of the deflection-angle prism 31 (31a and 31b) are selected so that the pitch P between two scenes on the film 21 in case of photographing the fundus (defective sight ametropy OD, working distance D) and the pitch P' in case of photographing the front portion of the eye by inserting the deflection-angle prisms 31(31a and 31b) correspond with each other. P' is an inter-image pitch whence the focusing is corresponded to the front portion of the average examinee's eye under the highly useful working distance D'

Observation Optical System

The observation optical system and the photographing optical system use the objective lens 13, the swing mirror 22 and the components between the objective lens 13 and the swing mirror 22 in common. When observing the fundus, the swing mirror 22 is set on the light path of the photographing optical system to reflect the observation light beam reflected by the fundus and passed through the components from the objective lens 13 through the focusing lenses 19a and 19b toward mirrors 23a and 23b. The observation light beam reflected by the mirrors 23a and 23b passes through observation image forming lenses 24a and 24b, focusing glasses 27a and 27b, and oculars 25a and 25b, and fall on the right eye 26a and the left eye 26b of the observer.

The operation of the stereoscopic retinal camera thus constructed will be described hereinafter.

The stereoscopic retinal camera is mounted on a movable table, not shown, which is moved relative to a fixed table by a sliding mechanism. The examinee's head is held on a head support fixed to the fixed table, and the halogen lamp 1 is turned on to illuminate the eye 14. In case of photographing the fundus of the eye, the observer operates the sliding mechanism to align the image of the aperture diaphragm 6 on the cornea with the pupil of the eye 14 so that the fundus is illuminated properly in proper working distance D. In case of photographing the front portion of the eye, the operator extends the working distance to D' from D. The illumination light is expanded wholly and the front portion of the eye is illuminated properly.

In case of photographing the fundus of the eye, the light beam reflected by the fundus is focused to form an inverted image of the fundus at the point A. The light beam passed the perforated mirror 12 is split into a right light beam and a left light beam by the two-hole diaphragm 15. The light beam splitting prism 16 disposed directly behind the two-hole diaphragm 15 interchanges the right light beam and the left light beam. Then, the light beams are deflected by the prisms 17a and 17b, and the deflected light beams are focused in erect images of the fundus at each point B and Ba on the film 21 by the pair of image forming lens systems including the relay lenses 18a and 18b, the focusing lenses 19a and 19b, and the image forming lenses 20a and 20b. The observer views the erect images for the stereoscopic observation of the fundus.

The observer turns the focusing knob during the binocular observation of the images to focus the focusing lenses 19a and 19b and makes the fine adjustment of the alignment of the image of the aperture diaphragm 6 with the pupil of the eye 14 so that flares of the illuminating light will not appear around the right and left images.

After the operations for aligning the image of the aperture diaphragm 6 with the pupil of the eye 14 and for focusing the focusing lenses 19a and 19b have been completed, a shutter release button is depressed. Then, the swing mirror 22 is lifted up and the xenon flash lamp 3 flashes synchronously to form the image of the fundus on the film 22.

As shown in FIG. 2, in case of photographing the front portion of the eye, the operator extend the working distance to D' from D which is the working distance when the fundus is photographed, the photographing area of the front portion of the eye is maintained properly. At that time the intermediate image is moved to plus side position A' from position A by the objective lens 13. Then the auxiliary lenses 30a and 30b are inserted into the optical path to compensate for lack of focus adjusting area of the image forming optical system by the focusing lenses 19a and 19b. By inserting the auxiliary lenses 30a and 30b, the front portion images B' and Ba' of the eye are formed on the film 21, as the inter-image pitch P' becomes narrower than the inter-image pitch P which is the pitch when the fundus is photographed, the operator may insert the deflection-angle prisms 31a and 31b into the optical path, whereby the inter-image pitch is extended to P (shown in FIG. 3). The operation being continued is almost same as the operation of photographing the eye's fundus, therefore the detail explanation of the operation is omitted.

The automatic operations of the stereoscopic retinal camera are controlled by the microcomputer mounted in the apparatus.

The present invention may be embodied in other specific forms without departing from the spirit or essential characteristics thereof. For instance, if the image forming optical system having the focus adjusting area sufficiently, the auxiliary lenses 30a and 30b are not necessary to be provided, and a concave lens is inserted into the optical path when the eye's fundus is photographed. Further, the deflection-angle prism is employed in this embodiment to accomplish the angle-correction of the optical axis with simple constitution, variety of constitutions well known for angle-correction, are able to be adopted.

Figure 4:
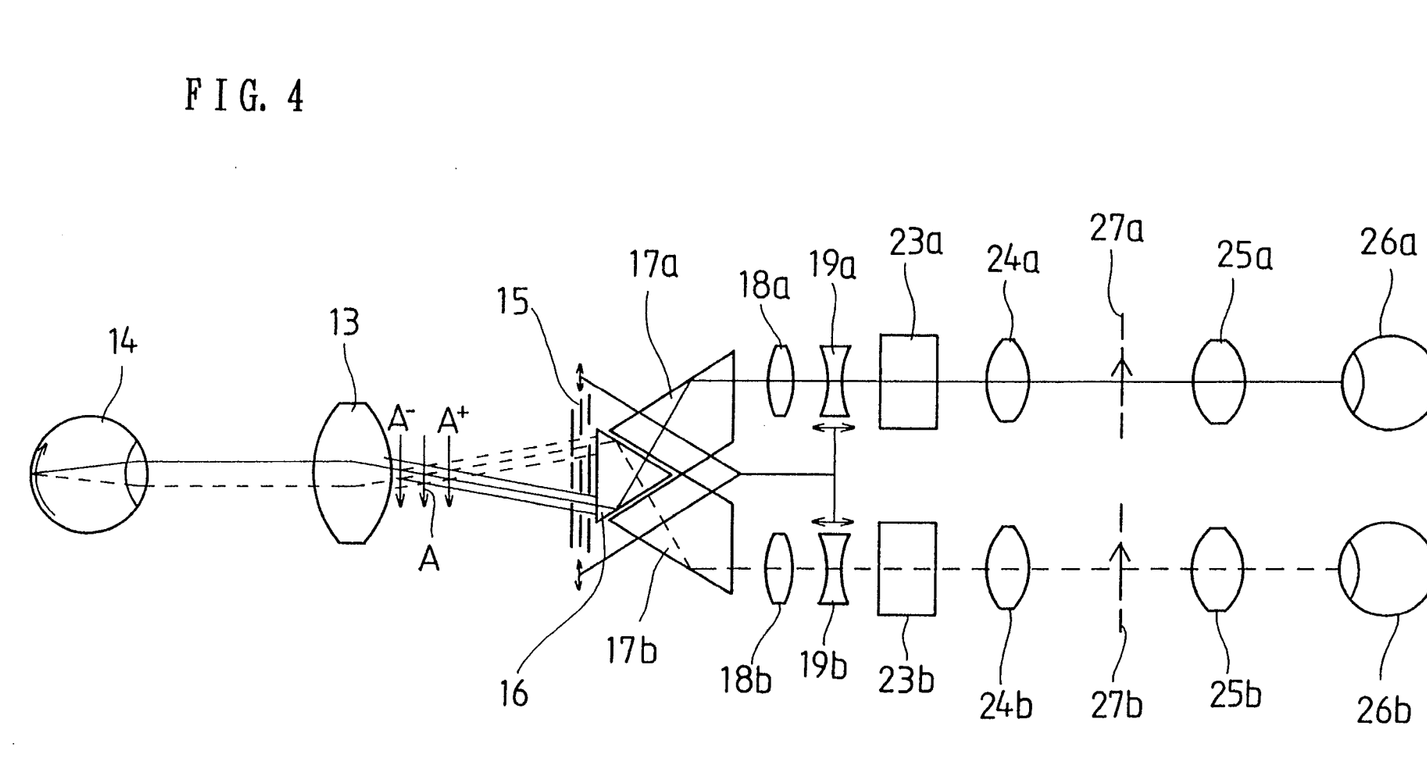
FIG. 4 is a diagrammatic top view of the optical systems of a stereoscopic retinal camera in a second embodiment according to the present invention, which explains a mechanism that a right and left apertures of two-hole diaphragms 15 (15a and 15b) are moved in synchronizing to focusing lenses 19 (19a and 19b)
Figure 5:
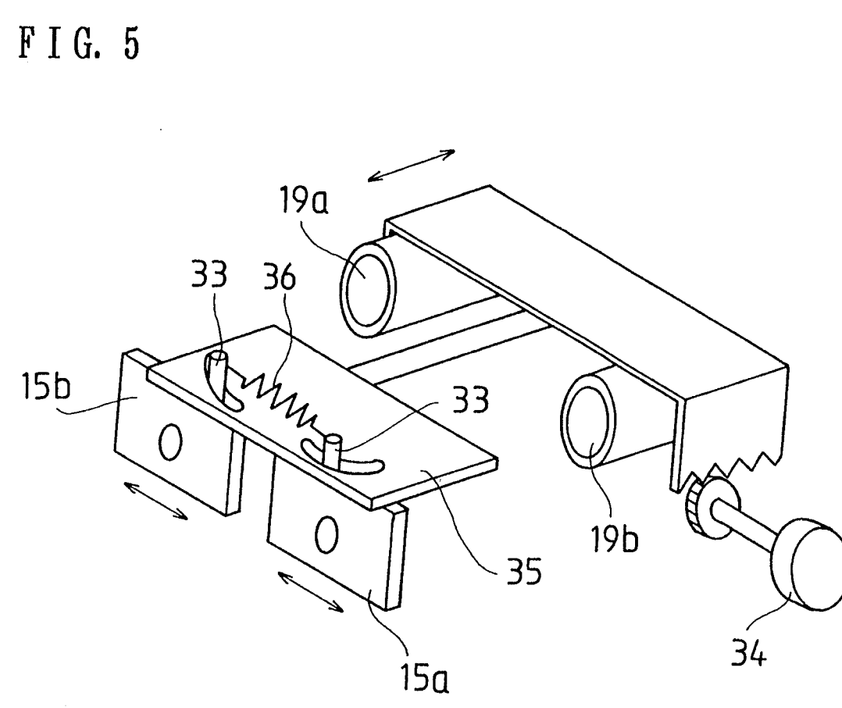
FIG. 5 is a partial diagrammatic view in perspective of the camera of FIG. 4.

In FIG. 4, there is shown the arrangement of the optical system in a second embodiment, and FIG. 5 shows a partial view in perspective of the optical system. The character of the second embodiment consists in the constitution of the two-hole diaphragm. The explanation of other part of the constitution is omitted, as it is already explained in the first embodiment.

The two-hole diaphragms 15 (15a and 15b) are disposed in a conjugate relation with the pupil of the examinee's eye with respect to the objective lens 13. Further, the right and left apertures of the respective two-hole diaphragms 15a and 15b is constituted as to be moved in synchronizing with the focusing lenses 19a and 19b. FIG. 5 shows the mechanism being synchronized mechanically, as one example. That is to say, the two-hole diaphragm 15 consists of a couple of aperture plates 15a and 15b, having pins 33, 33 thereon respectively. The aperture plates 15a and 15b are pulled toward each other by a spring 36 which is connected to the pins 33, 33. When the focusing lenses 19a, 19b are moved toward front and rear direction by operating a diopter adjusting knob 34, the pins 33, 33 are moved to be away or come near along a guide groove (not shown in FIG. 5) which is formed on a side of a guide plate 35, the aperture plates 15a, 15b are moved to an arrow direction shown in FIG. 5, whereby the distance between center points of both apertures of the aperture plates 15a, 15b is changed. The quantity of movement is determined according to the moving distance of the first intermediate image formed by refracting power of the examinee's eye. The shape of the guide groove is formed in relation to the moving quantity of the focusing lenses 19a, 19b, so that the ratio of distance between the two-hole diaphragms 15a, 15b and the distance from the two-hole diaphragms 15a, 15b to the intermediate image is fixed.

In that case, it is not necessary to connect the movement of the focusing lenses 19a, 19b and the center distance of the apertures of the aperture plates 15a, 15b, it is proper to provide the moving mechanism of the aperture plates 15a, 15b by detecting the moving quantity of the focusing lenses 19a, 19b by using a shaft encoder or the like.

The mechanism of controlling two movements such as mentioned above is known variously, therefore the explanation of the mechanism is omitted, but the present invention is not intended to be limited.

In case of the above second embodiment, the two-hole diaphragms 15a, 15b are moved to separate each other synchronizing to the movement of the focusing lenses 19a, 19b, the same effect is obtained by the mechanism that the two-hole diaphragms 15a, 15b move to the same direction and same distance of the movement of the first intermediate image A along the optical axis. This embodiment is shown in FIG. 6.

Figure 6:
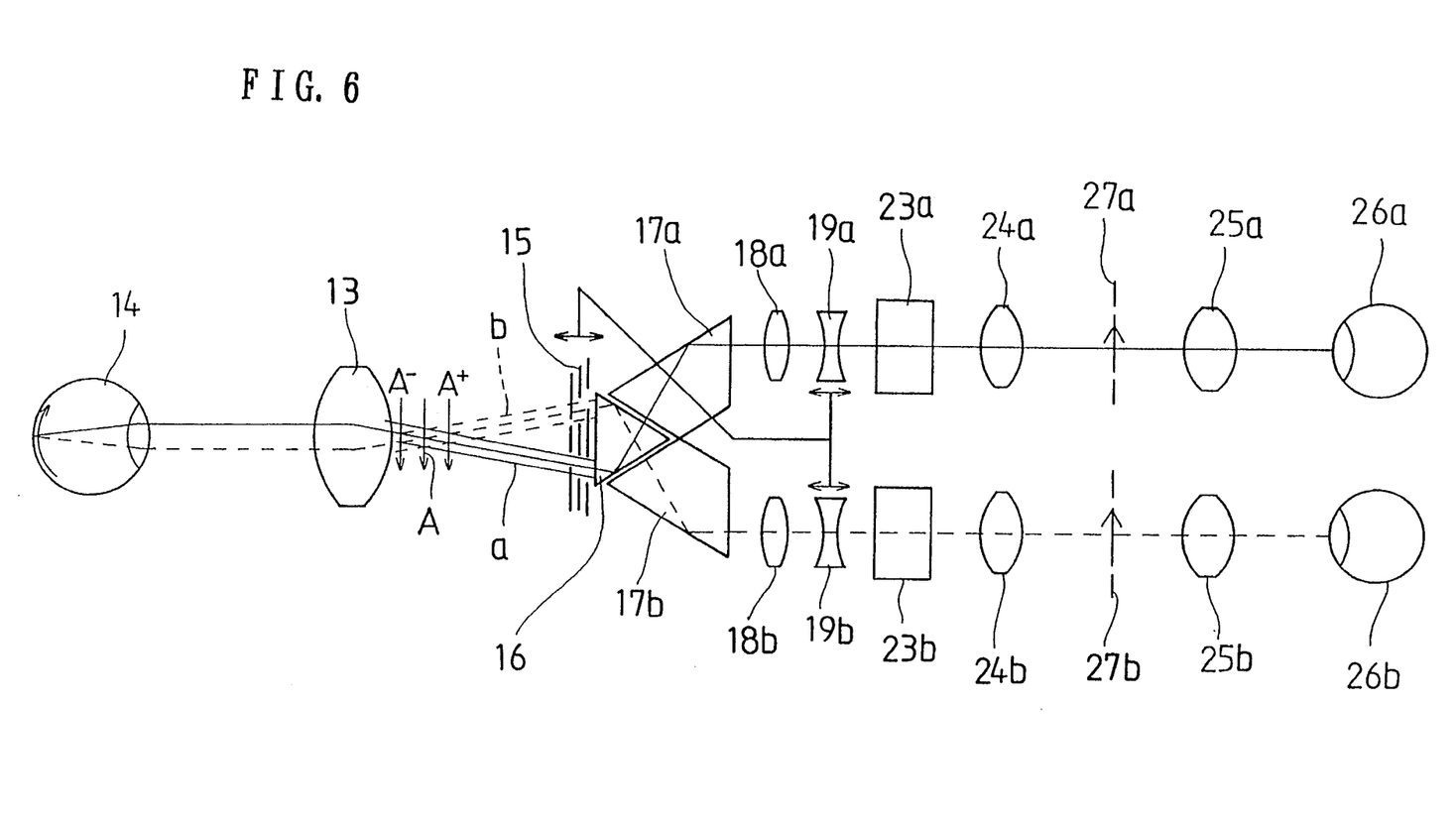
FIG. 6 is also a diagrammatic top view of the optical systems of the stereoscopic retinal camera shown in FIG. 4, which explains a mechanism that the two-hole diaphragms 15 (15a and 15b) are moved according to the movement of an intermediate image A toward a direction of the optical axis.

In this FIG. 6, the above mentioned two-hole diaphragms 15a, 15b are moved to the front and rear direction (i.e. optical direction) along the optical path by synchronizing with the movement of the focusing lenses 19a, 19b for focusing the lens according to the refracting power of the examinee's eye. That is to say, the two-hole diaphragms 15a, 15b are moved to the objective lens 13 when the refracting power is on near sightedness side and are moved to the light beam splitting prism 16, 17a, 17b side respectively, and the quantity of the movement of the two-hole diaphragms are determined to be equal to the quantity of the movement of the first intermediate image which is moved according to the refracting power of the examinee's eye, whereby the stereoscopic angle faced to the first intermediate image against the optical axis a and b, is always hold constant. And because the stereoscopic angle is held constant, the change of the pitch between two images on the film 21 is also able to stay small.

Further, according to each of the above mentioned embodiments, the change of the stereoscopic visual angle is amended against the defective sight ametropy perfectly, but it is able to add the modification, for example, to amend the angle by degrees in a certain permission range, without departing from the spirit and the scope of the invention. And also it is purposeful to combine the mechanism of the above mentioned second embodiment with the mechanism of the above mentioned first embodiment.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A stereoscopic retinal camera which enables at least one of the stereoscopic observation of the fundus of the eye and the production of a stereoscopic picture of the fundus and a front portion of the eye by dividing a light beam reflected by the fundus into two light beams and transmitting the two light beams respectively along the light paths of separate image forming optical systems, said stereoscopic retinal camera comprising:

a focus adjustment means for photographing the fundus and the front portion of the eye; and an optical correction means for correcting an inter-image pitch between a right image and a left image so as to be correspondent when at least one of the fundus and the front portion of the eye is photographed by operating said focus adjustment means;

wherein said focus adjustment means comprises an auxiliary optical system for changing a focus area from the front portion of the eye to the fundus or from the fundus to the front portion of the eye; and wherein said auxiliary optical system has a refracting power corresponding to a difference between the refracting power of an average eye and the refracting power of the front portion of the average eye.

2. A stereoscopic retinal camera according to claim 1 wherein said optical correction means is a deflective optical system for changing a direction of the light beams.

3. A stereoscopic retinal camera according to claim 2, wherein said deflective optical system has a prism function to compensate a difference of inter-image pitch between a right image and a left image when photographing the fundus of an average eye and the front portion thereof.

4. A stereoscopic retinal camera according to claim 3, wherein said deflective optical system is a deflection-angle prism.

5. A stereoscopic retinal camera which enables at least one of the stereoscopic observation of the fundus of the eye and the production of a stereoscopic picture of the fundus by dividing a light beam reflected by the fundus along an optical path into two light beams and transmitting the two light beams respectively along light paths of separate image forming optical systems, said stereoscopic retinal camera comprising:

a focus adjustment means disposed in the image forming optical system in a conjugate relation with the fundus and the photographing position; and an optical correction means for correcting a difference of a stereoscopic visual angle accompanying the operation of said focus adjustment means;

wherein said optical correction means comprises a moving means for moving a two-hole diaphragm for determining a stereoscopic visual angle toward the optical path.

6. A stereoscopic retinal camera according to claim 5, wherein said optical correction means comprises a mechanism which moves by synchronizing with said focus adjustment means.

7. A stereoscopic retinal camera which enables at least one of the stereoscopic observation of the fundus of the eye and the production of a stereoscopic picture of the fundus by dividing a light beam reflected by the fundus along an optical path into two light beams and transmitting the two light beams respectively along light paths of separate image forming optical systems, said stereoscopic retinal camera comprising:

a focus adjustment means disposed in the image forming optical system in a conjugate relation with the fundus and the photographing position; and an optical correction means for correcting a difference of a stereoscopic visual angle accompanying the operation of said focus adjustment means;

wherein said optical correction means comprises a variation means for changing a distance between two-holes of a couple of two-hole diaphragms for determining a stereoscopic visual angle.

8. A stereoscopic retinal camera according to claim 7, wherein said optical correction means comprises a mechanism which moves by synchronizing with said focus adjustment means.

9. A stereoscopic retinal camera comprising:

an objective lens for directing a light beam reflected from an examinee's eye along an optical path, wherein the objective lens focuses the reflected light beam to a first point A when the examinee's eye is at a first position located a first distance D from the objective lens, and further focuses the reflected light beam to a second point A' when the examinee's eye is at a second position located a second distance D' from the objective lens;

optical means for splitting the reflected light beam into a right light beam and a left light beam and for respectively directing the right light beam and the left light beam to a right optical path and a left optical path;

focusing means, located in the right and left optical paths, for focusing the right light beam and the left light beam to form a first set of stereoscopic images at a first image point B and a second image point Ba on a film plane when the objective lens focuses the reflected light beam to the first point A, wherein the first set of stereoscopic images have an inter-image pitch P, and for focusing the right light beam and the left light beam to form a second set of stereoscopic images at a third image point B' and a fourth image point Ba' on the film plane when the objective lens focuses the reflected light beam to the second point A', wherein the second set of stereoscopic images have an inter-image pitch P' that is different from the inter-image pitch P of the first set of stereoscopic images; and optical correction means that can be selectively placed in the right and left optical paths, wherein the optical correction means causes the inter-image pitch P' of the second set of stereoscopic images to be corrected to the inter-image pitch P of the first set of stereoscopic images, wherein the second set of stereoscopic images are formed at the first and second image points B, Ba.

10. A stereoscopic camera as claimed in claim 9, wherein the first set of stereoscopic images are images of the fundus of the examinee's eye and the second set of stereoscopic images are images of a front portion of the examinee's eye.

11. A stereoscopic camera as claimed in claim 9, wherein the optical correction means is a deflective optical system.

12. A stereoscopic camera as claimed in claim 11, wherein the deflective optical system includes a deflection-angle prism.

13. A stereoscopic camera as claimed in claim 9, further comprising an illuminating optical system for illuminating the examinee's eye with an illumination light beam.

14. A stereoscopic camera as claimed in claim 9, further comprising an observation optical system for selectively receiving the first and second sets of stereoscopic images.

15. A stereoscopic camera as claimed in claim 9, wherein the focusing means includes an auxiliary focusing means that can be selectively placed in the right and left optical paths when the objective lens focuses the reflected light beam to the second point A'.

16. A stereoscopic camera as claimed in claim 15, wherein the auxiliary focusing means comprises auxiliary lenses.

17. A stereoscopic camera as claimed in claim 9, wherein the optical correction means has a predetermined optical correction factor that corresponds to the correction factor necessary to correct the inter-image pitch P' of the second set of stereoscopic images to the inter-image pitch P of the first set of stereoscopic images for an average eye.

18. A stereoscopic retinal camera which enables at least one of the stereoscopic observation of the fundus of the eye and the production of a stereoscopic picture of the fundus of the eye by dividing a light beam reflected by the fundus into two light beams and transmitting the two light beams respectively along the light paths of separate image forming optical systems, said stereoscopic retinal camera comprising:
  a focus adjustment means for photographing the fundus and the front portion of the eye; and
  an optical correction means for correcting an inter-image pitch between a right image and a left image so as to be correspondent when at least one of the fundus and the front portion of the eye is photographed by operating said focus adjustment means;
  wherein said focus adjustment means comprises an auxiliary optical system for changing a focus area from the front portion of the eye to the fundus or from the fundus to the front portion of the eye.

* * * * *